(12) United States Patent
Mallender et al.

(10) Patent No.: US 9,989,446 B2
(45) Date of Patent: Jun. 5, 2018

(54) SAMPLE PRESERVATION METHOD AND SAMPLE APPLICATION SUBSTRATE

(75) Inventors: Philip Robert Mallender, Maidstone (GB); Douglas Mark Green, Maidstone (GB); Sarah Janet Clegg, Maidstone (GB); Barry Edmund Johnson, Maidstone (GB); Jimmy Hedin Dahlstrom, Uppsala (SE); Mattias Algotsson, Uppsala (SE); Ronnie Palmgren, Uppsala (SE)

(73) Assignee: GE HEALTHCARE UK LIMITED, Little Chalfont (GB)

( * ) Notice: Subject to any disclaimer, the term of this patent is extended or adjusted under 35 U.S.C. 154(b) by 165 days.

(21) Appl. No.: 13/985,360

(22) PCT Filed: Feb. 27, 2012

(86) PCT No.: PCT/SE2012/050211
§ 371 (c)(1),
(2), (4) Date: Aug. 14, 2013

(87) PCT Pub. No.: WO2012/118428
PCT Pub. Date: Sep. 7, 2012

(65) Prior Publication Data
US 2013/0330751 A1    Dec. 12, 2013

(30) Foreign Application Priority Data
Feb. 28, 2011 (GB) .................................. 1103363.6

(51) Int. Cl.
| | | |
|---|---|---|
| G01N 1/28 | (2006.01) | |
| D21H 11/20 | (2006.01) | |
| D21H 17/18 | (2006.01) | |
| D21H 27/08 | (2006.01) | |

(52) U.S. Cl.
CPC ............... *G01N 1/28* (2013.01); *D21H 11/20* (2013.01); *D21H 17/18* (2013.01); *D21H 27/08* (2013.01)

(58) Field of Classification Search
CPC .......... G01N 1/28; D21H 11/20; D21H 17/18; D21H 27/08
See application file for complete search history.

(56) References Cited

U.S. PATENT DOCUMENTS

| | | | |
|---|---|---|---|
| 3,645,692 A | | 2/1972 | Stork et al. |
| 4,308,187 A | * | 12/1981 | Van Eenam ............ C08L 27/06 162/168.1 |
| 5,114,538 A | | 5/1992 | Malatesta |
| 5,143,583 A | * | 9/1992 | Marchessault et al. ...... 162/138 |
| 5,439,591 A | * | 8/1995 | Pliura et al. .................. 210/635 |
| 5,652,348 A | * | 7/1997 | Burton et al. .................. 536/20 |
| 5,955,582 A | * | 9/1999 | Newman et al. .......... 530/387.1 |
| 6,309,887 B1 | | 10/2001 | Ray |
| 2004/0019196 A1 | | 1/2004 | Bair, Jr. et al. |
| 2006/0014177 A1 | * | 1/2006 | Hogan .................... A61K 38/02 435/6.14 |
| 2006/0014298 A1 | * | 1/2006 | Shirley et al. ................ 436/174 |
| 2010/0243187 A1 | * | 9/2010 | Runge et al. ............... 162/164.4 |
| 2012/0208986 A1 | * | 8/2012 | Wenger et al. ............ 530/388.4 |
| 2013/0217866 A1 | * | 8/2013 | Falkenstein et al. ...... 530/389.1 |

FOREIGN PATENT DOCUMENTS

| | | |
|---|---|---|
| EP | 0 348 127 A2 | 6/1989 |
| GB | 2016473 | 9/1979 |
| GB | 2043734 | 10/1980 |
| JP | 10-160725 A | 6/1998 |
| JP | 2001-228153 A | 8/2001 |
| JP | 2004-144636 A | 5/2004 |
| WO | WO 00/34584 | 6/2000 |

OTHER PUBLICATIONS

GE Healthcare Life Science, CaptoTM MMC ImpRes, 28 pages, 2013, retrieved from https://www.gelifesciences.com/gehcls_images/GELS/Related%20Content/Files/1363346133489/litdoc29027184_20130315211607.pdf on Aug. 10, 2014.*
Bergqvist, Y., et al., Journal of Chromatography B, vol. 719, No. 1-2, pp. 141-149, 1998.
Van Der Heijdena, J., et al., Journal of Pharmaceutical and Biomedical Analysis, vol. 50, No. 4, pp. 664-670, 2009.
Blessborn, D., et al., Journal of Pharmaceutical and Biomedical Analysis, vol. 45, No. 2, pp. 282-287, 2007.
Japanese Office Action for JP Application No. 2013-556579 dated Mar. 1, 2016 (3 pages).

* cited by examiner

*Primary Examiner* — Andrea S Grossman
(74) *Attorney, Agent, or Firm* — Eversheds Sutherland (US) LLP (57) ABSTRACT

The invention discloses a sample preservation method which comprises the following steps: a) providing a paper substrate comprising ligands, where the ligands comprise charged groups, b) applying a sample comprising at least one analyte and at least one contaminant on the paper substrate, c) drying the sample on the paper substrate and, d) extracting at least part of the paper substrate to provide a solution of the analyte.

20 Claims, 5 Drawing Sheets

SAMPLE PRESERVATION METHOD AND SAMPLE APPLICATION SUBSTRATE

CROSS-REFERENCE TO RELATED APPLICATIONS

This application is a filing under 35 U.S.C. 371 of international application number PCT/SE2012/050211, filed Feb. 27, 2012, published on Sep. 7, 2012 as WO 2012/118428, which claims priority to patent application number 1103363.6 filed in Great Britain on Feb. 28, 2011.

TECHNICAL FIELD OF THE INVENTION

The present invention relates to methods for sample preservation, and more particularly to sample preservation on paper substrates. The invention also relates to paper substrates for sample preservation and to methods of manufacturing such substrates.

BACKGROUND OF THE INVENTION

Increasing use is being made of paper substrates in the analysis and/or storage of biological materials. One such area of use concerns the growing need for rapid analysis of large quantities of blood samples in pharmacokinetic research, for example in drug discovery programmes. It is obviously desirable for such uses that the paper combines satisfactory mechanical properties with an ability to hold the biological material of interest in such a way that it can be subjected to analysis and/or further processing following storage. Examples of such papers are those known as FTA and FTA Elute (Whatman, part of GE Healthcare) described for example in U.S. Pat. Nos. 5,756,126 and 5,939,259. These papers have been impregnated with chemicals to provide sample preservation and to facilitate further processing of certain analytes, in particular nucleic acids.

However, in addition, it is necessary that, while held on the paper or after extraction, the analyte can be subjected to suitable analytical techniques, such as mass spectroscopy or immunoassays without interference in the process from any chemical constituents that may have been included in the coating on the paper. Thus, for example, the coatings used for suitable papers, such as those sold as FTA and FTA Elute, differ in composition and it is therefore necessary to bear in mind the nature of these chemicals and select carefully a suitable combination of substrate, analyte and analysis method. For samples such as blood, the analytes being detected, e.g. a drug being tested, may be present in very small quantities which are readily masked in the presence of certain coating chemicals. Further, many pharmaceutically important analytes, in particular proteins and other biomacromolecules are highly sensitive to denaturation, degradation and other disruptive events which lead to loss of recovery and/or loss of biological activity.

Chemicals introduced for stabilisation of nucleic acids do not necessarily provide stabilisation of proteins—in some cases they may even be detrimental to protein stability.

Cellulose fibres substituted with charged groups have been described in GB2016473A and WO2003016356. There is however no suggestion of using these fibres in preservation of biological samples and the substitution reactions are performed under conditions that cause substantial degradation of the fibres, making them unsuitable for industrial manufacture of paper. No data from continuous-web paper machines are presented.

It is therefore desirable to use substrates with sample-preserving treatments in which no chemicals are in a position to interfere with the analysis. Plain untreated cellulose papers such as the 903 or 31ETF papers (Whatman, part of GE Healthcare) are used for preservation of blood samples, but do not always give the desirable analytical recoveries and biological activities of e.g. sensitive proteins. Accordingly there is a need for sample preservation methods and sample preservation substrates with improved performance.

SUMMARY OF THE INVENTION

One aspect of the invention is to provide solutions of stored samples with high recovery of biologically active analyte and reduced concentrations of contaminants. This is achieved with a method as defined in claim 1.

One advantage is that a high recovery of sensitive protein analytes can be obtained. Further advantages are that interference from e.g. phospholipid contaminants can be reduced and that homogeneous sample spots can be formed on the paper substrate.

Another aspect of the invention is to provide a substrate capable of receiving a sample and after drying rendering a solution with high recovery of biologically active analyte and reduced concentrations of contaminants. This is achieved with a sample application substrate as defined in claim 22.

A further aspect of the invention is to provide a method of preparing a functional paper substrate capable of receiving a sample and after drying of the sample rendering a solution with high recovery of biologically active analyte and reduced concentrations of contaminants. This is achieved with a method as defined in claim 29.

Further suitable embodiments of the invention are described in the dependent claims.

DEFINITIONS

The term "paper" as used herein means a fibrous web or sheet material. Paper comprises fibres, e.g. cellulose or glass fibres, and optionally other components, such as e.g. particulate fillers, wet strength or dry strength additives, retention agents etc.

The term "analyte" as used herein means a substance undergoing or intended to undergo detection, quantification, analysis, characterisation and/or evaluation.

The term "contaminant" as used herein means a substance having the potential to interfere with the detection, quantification, analysis, characterisation or evaluation of one or more analytes. An analyte can also be a contaminant if it has the potential to interfere with the detection, quantification, analysis, characterisation or evaluation of another analyte.

The term "sample" as used herein means a portion of a fluid, liquid, semisolid or solid material.

The term "ligand" as used herein means a chemical species capable of binding or attracting another species. If a ligand is attached to a solid surface, dissolved substances may bind to or be retained by the surface, depending on the selectivity of the ligand for each substance.

DETAILED DESCRIPTION OF EMBODIMENTS

In one aspect the present invention discloses a sample preservation method which comprises the following steps:

a) providing a paper substrate comprising ligands, where said ligands comprise charged groups, b) applying a sample comprising at least one analyte and at least one contaminant on said paper substrate, c) drying said sample on said paper substrate and, d) extracting at least part of said paper substrate to provide a solution of said analyte.

In other words, a sample comprising at least one analyte and at least one contaminant is applied to a functional paper substrate and dried. A portion of the paper substrate or the entire paper substrate is then extracted to produce a solution containing the analyte or analytes. The functional paper substrate comprises chemically introduced ligands, which in their turn comprise charged groups. The paper substrate may be in the form of a card, optionally with one or more designated sample application areas, indicated by e.g. a printed pattern. It may also comprise indices for identification of the sample(s) applied, e.g. text, bar codes, RFID tags etc. The sample may be a liquid, which can be absorbed by the paper substrate and form a sample spot. It may also be a solid or semi-solid tissue sample, in which case it can be pressed to and/or macerated on the paper substrate so that fluid components are absorbed and form a sample spot. The drying can be performed actively, e.g. by applying heat, dry air or vacuum or it can be performed passively by waiting until fluid components have evaporated. The drying can proceed until the moisture content of the paper substrate is in equilibrium with the ambient atmosphere (typically up to 10% moisture in the paper at relative humidities below 80%) or until about 50% or more of the volatile components in the sample have evaporated. The extraction can be performed e.g. by soaking a portion of the paper substrate in an excess of aqueous or non-aqueous liquid, where the choice of liquid and soaking conditions will depend on the nature of the analyte(s) and on the demands of any analytical methods that may be used subsequently.

The ligands may comprise positively charged groups such as protonated amines, quaternary ammonium groups, amidines, sulfonium groups etc. and/or negatively charged groups such as carboxylates, sulfonates, sulfates, phosphates, phosphonates etc. Non-limiting examples of ligands comprising charged groups include diethylaminoethyl —$CH_2CH_2N^+H(CH_3CH_2)_2$, trimethylammonium —$N^+(CH_3)_3$, carboxymethyl —$CH_2COO^-$, sulfoethyl —$CH_2CH_2SO_3^-$ and sulfopropyl —$CH_2CH_2CH_2SO_3^-$, as well as more complex structures such as multi-modal ligands or zwitterionic ligands.

In some embodiments, the method also comprises a step c') of storing the paper substrate with the dried sample for at least 24 h, such as at least one week or at least one month. This step can suitably be performed between steps c) and d) and is important for the convenience of the method. Having a high storage stability means that a multitude of samples can be collected and analysed at a later stage and they can also conveniently be transported to e.g. a central analysis facility. The storage can take place at room temperature (about 20-25° C.) or under refrigeration (e.g. about 4-8° C.), depending on the stability of the analyte(s) in each specific case. From a cost and logistics point of view it is advantageous if the analyte can be recovered with high recovery and high biological activity from the substrate after storage at room temperature or even at temperatures up to about 37° C. or 40° C. which may e.g. occur under tropical conditions.

In certain embodiments, the method also comprises a step c") of punching or cutting out one or more pieces of predetermined area from the paper substrate with the sample and in step d) extracting the substrate piece(s). This step may be performed between step c) or c') and step d) and adds the possibility of performing several different or parallel analyses of the same sample spot and also adds the possibility of performing quantitative analyses independent of the sample size. The area of the punched/cut out piece multiplied with the paper thickness defines a particular volume and, provided that the sample is absorbed homogeneously by the paper substrate, the amount of analyte(s) in that particular volume can be used to calculate the concentration in the original sample. One advantage of the method of the invention is that high recoveries of analytes can be obtained, which is essential in quantitative analyses. Another advantage is that a homogeneous distribution of analytes over the entire sample spot can be obtained, which is also a prerequisite for quantitative analyses.

In some embodiments, the method also comprises a step c''') of washing said paper substrate. This step may typically be performed between step c) and d) (e.g. after step c') and/or c") and adds a possibility of removing contaminants. It can e.g. be performed by soaking a portion of the paper substrate in a suitably selected aqueous or non-aqueous washing liquid. A particularly efficient removal of contaminants may take place if one or more analytes bind to the functional paper substrate during the washing conditions, while one or more contaminants are washed off. In this case, it can be advantageous to change the conditions during the extraction in step d) so that the analyte(s) are desorbed from the substrate. The nature of the washing and extraction liquids is selected according to the characteristics of the paper substrate, the analyte(s) and the contaminant(s). As a rule of thumb, aqueous or partly aqueous liquids, such as buffers, can be used with proteinaceous analytes, with low salt contents promoting binding between the ligands comprising charged groups and analytes having a net opposite charge to the charged groups and high salt contents promoting binding between hydrophobic groups and analytes.

In certain embodiments, the method also comprises a step e) of analyzing the solution obtained in step d) with respect to the concentration, structural integrity and/or biological activity of the analyte(s). Methods used in this step can be e.g. mass spectrometry, an immunoassay or a biological assay. Examples of immunoassays contemplated are enzyme-linked immunosorbent assays (ELISA), radioimmunoassays, magnetic immunoassays, lateral flow assays, Western blotting etc. Biological assays are typically used to assess biological activities of substances and can be e.g. various forms of cell assays or animal tests.

In some embodiments, the ratio of analyte concentration to total contaminant concentration in the solution provided in the extraction step d) is at least about twice as high, such as at least about ten times as high, as in the original sample. This relative enrichment of analyte can be achieved by selective binding of contaminants to the substrate during the extraction and/or by selective binding of analyte(s) to the substrate during a washing step.

In certain embodiments the sample comprises a biological fluid, e.g. blood, serum, plasma, cerebrospinal fluid, urine, cell culture supernatant, plant sap etc. The method of the invention is particularly suited for preservation and preparation of complex biological fluid samples, which contain numerous contaminants and where analyte concentrations are often many orders of magnitude lower than the contaminant concentrations. Biological fluids often contain species that are highly sensitive to degradation and/or denaturation and it is thus essential that a substrate allowing for high recoveries of biologically active analytes is used.

In some embodiments the contaminants comprise phospholipids. Phospholipids are a common contaminant in blood and in any sample containing cells or cell debris. They are viscous hydrophobic materials that interfere with many analytical methods, in particular mass spectrometry that is commonly used in pharmacokinetic analyses. An advantage of the method of the invention is that it is suitable for removing phospholipids from samples. In one embodiment the ratio of analyte concentration to total phospholipids concentration in the solution provided in step d) is at least about twice as high as in the original sample.

In certain embodiments one or more analyte(s) is/are charged, with a net charge opposite to the charged groups in the ligands. An advantage of this is that the storage stability of sensitive proteinaceous analytes is improved. A further advantage is that contaminants can be washed off in a washing step. The sign of the net charge of an analyte can in many cases be calculated from the chemical structure of the analyte. For proteinaceous and other amphoteric analytes the net charge is typically positive at pH values below the isoelectric point and negative at pH values above the isoelectric point. Isoelectric points have been published for many proteins and may also be determined by e.g. isoelectric focusing electrophoretic methods.

In some embodiments one or more analyte(s) is/are charged, with a net charge of the same sign as the charged groups in the ligands. An advantage of this is that extraction recoveries may be increased and that an improved spot homogeneity may be achieved.

In certain embodiments one or more analyte(s) comprise(s) a protein, such as a biopharmaceutical. Particular proteins of interest include immunoglobulins such as monoclonal antibodies, enzymes, protein hormones such as erythropoietins, insulin etc. and different groups of biomarkers.

In some embodiments at least one contaminant comprises charged groups, with a net charge opposite to the charged groups comprised in the ligands. An advantage of this is that it is easier to device conditions for extraction where contaminants are retained on the paper and analytes are extracted. This can also apply to zwitterionic contaminants, which comprise both positively and negatively charged groups.

In some embodiments step a) also comprises reacting a base paper with a ligand precursor reagent to provide a paper substrate comprising ligands. The base paper can be a plain, non-functional paper or it can be a paper that has been activated by treating it with an activating reagent before the reaction with the ligand precursor. Typical activating reagents are electrophiles able to react with hydroxyl groups in the paper and producing a reactive group for subsequent reaction. Examples of activating reagents include epichlorohydrin and diepoxides (producing reactive epoxy groups), allyl glycidyl ether and allyl halides (producing reactive allyl groups), divinyl sulfone (producing reactive vinyl sulfone groups), tosyl and tresyl chlorides (producing reactive tosylates/tresylates) etc. Examples of ligand precursor reagents able to react directly with hydroxyl groups are organic halides, e.g. diethylaminoethyl chloride, 2-bromoethane sulphonic acid sodium salt and 2-bromoacetic acid; epoxides, e.g. glycidyl trimethylammonium chloride and reactive vinyls, e.g. vinyl sulphonic acid sodium salt. Examples of ligand precursor reagents able to react directly with silanol hydroxyls on e.g. glass fibre paper include functional alkoxysilanes and chlorosilanes. Examples of ligand precursor reagents able to react with epoxies, vinyl sulfones and tosylates/tresylates on activated papers include e.g. amines and thiols. Examples of ligand precursor reagents able to react with allyls on activated papers includes e.g. thiols and polymerizable unsaturated monomers. Polymerizable monomers comprising charged groups may be graft polymerized onto the base paper either by copolymerization with allyls or other unsaturated groups on the paper, by chain transfer reactions to e.g. thiols on the paper or by intitiation from the paper, e.g. in cerium grafting or ATRP grafting methods.

In some embodiments step a) further comprises reacting a fibre pulp with a ligand precursor reagent to obtain essentially intact fibres comprising covalently bound ligands and then on a continuous-web paper machine forming a paper web comprising at least 90 wt % of said essentially intact fibres with covalently bound ligands. The ligand precursor reagents and papermaking conditions can be as discussed below under the aspect disclosing a method of preparing a functional paper.

In certain embodiments the paper substrate also comprises groups which are capable of non charge-charge interactions with one or more analyte(s). These groups can be part of the ligands, in which case the ligands may be denoted multimodal or mixed-mode ligands, and/or be separately attached to the paper fibres. The non charge-charge interactions may comprise hydrophobic interactions, electron acceptor-donor interactions, and/or thiophilic interactions Electron donor-acceptor interactions include interactions such as hydrogen-bonding, π-π, cation-π, charge transfer, dipole-dipole, induced dipole etc. An advantage of using groups capable of non charge-charge interactions is that high recoveries and high stabilities of proteinaceous analytes can be obtained. Examples of groups capable of hydrophobic interactions include e.g. aromatic or heteroaromatic rings and C4-C18 hydrocarbon chains. Hydrogen bonding can be obtained with e.g. hydroxyls, ethers, amines etc. Examples of groups capable of thiophilic interactions include e.g. sulfones and thioethers, while cation-pi interactions can be obtained with e.g. aromatic ring structures.

In some embodiments the ligands further comprise one or more aromatic or heteroaromatic ring structures and/or C4-C18 saturated or unsaturated, linear, branched or alicyclic hydrocarbon chains. The hydrocarbon chains can be substituted or interrupted by heteroatoms such as ether, hydroxyl or carbonyl oxygens, amine or amide nitrogens and/or thioether, thiol or sulphonyl sulphurs. Specific examples of ligands with such structures are alkyl and aryl amines such as tertiary N-aryl or N-alkylaryl amines, e.g. N-benzyl-N-methylethanolamine and N,N-dimethylbenzylamine (which may be coupled via the amine nitrogen to create a quaternary ammonium group) and ligands comprising an aromatic or heteroaromatic ring structure linked to a negatively charged group via a linker structure, e.g. N-benzoyl homocysteine (which may be coupled via the thiol group).

In certain embodiments the ligands are covalently bound to cellulose or glass fibers. The ligands can be bound directly to the fibres or via spacer or extender structures. Spacers are relatively short (e.g. with a chain length less than about 15 atoms) structures that may either be deliberately introduced during coupling or are introduced as a consequence of the particular activation and/or coupling chemistry used. Extenders are longer chain structures (e.g. polymers), typically introduced to increase the availability of the ligands. Cellulose fibres display large numbers of carbon-bound hydroxyl groups, which can react with electrophilic reagents as described above or be activated and reacted with other types of reagents. Glass fibres display silicon-bound hydroxyl groups (silanols) which can react in a similar way as the carbon-bound hydroxyls, but they are also conveniently modified with functional alkoxysilanes or chlorosilane reagents. Many varieties of cellulose fibres can be used, such as cotton, various grades of wood pulp, flax, hemp, ramie, regenerated cellulose fibres, bacterial celluloses etc. The cellulose fibres can be fibrillated before or during paper manufacture to obtain a suitable paper structure.

In some embodiments the paper substrate comprises at least about 50 micromol/g, such as at least 86 micromol/g, at least about 200 micromol/g, at least about 500 micromol/g or at least about 900 micromol/g ligands. The ligand content of the paper substrate can also be between 50 and 2000 micromol/g, such as between 86 and 2000 micromol/g, between 200 and 2000 micromol/g, between 900 and 2000 micromol/g or between 200 and 1000 micromol/g. These ligand contents are calculated on the dry weight of the paper and can be determined e.g. by well known titration methods (e.g. as the chloride ion capacity for ligands comprising positively charged groups or as the hydrogen ion capacity for ligands comprising negatively charged groups), from the adsorption capacity of easily detected charged species (e.g. dyes), by elemental analysis of e.g. heteroatoms or by spectroscopic methods such as e.g. NMR spectroscopy.

In certain embodiments the charged groups are positively charged or negatively charged over at least part of the pH 5 to pH 9 interval, such as over at least part of the pH 6 to pH 8 interval. Many biological samples have a more or less neutral pH and it is an advantage if the groups are charged at the pH of the sample applied. Some groups are charged over the entire pH interval, e.g. quaternary ammonium groups, sulfonate groups and sulphate groups, while other groups are charged above or below certain pH values, e g amines, carboxylic acids etc. The ligands may also comprise both positively and negatively charged groups, e.g. amphoteric or zwitterionic groups such as amino acids, betaines, sulfobetaines, phosphatidyl cholines etc.

In one aspect the present invention discloses a sample application substrate that comprises a sheet of paper with chemically introduced ligands comprising charged groups and with at least one designated sample application area. The paper can be in a card format, with or without cover or frame structures, and the sample application area can be indicated e.g. by a printed or embossed pattern. The sample application substrate of the invention is useful for sample preservation and sample pre-treatment methods e.g. according to the embodiments described above. The sample application substrate may also comprise further features, e.g. indices for identification of the sample(s) applied, e.g. text, bar codes, RFID tags etc. and/or means to indicate if a sample has been applied to a particular sample area or not (e.g. a dye indicator). The paper can e.g. have a dry weight of 175 to 195 g/m2 and a thickness of 470 to 570 microns (at a gauge pressure of 53 kPa).

In certain embodiments the sample application substrate comprises at least 50 micromol/g, such as at least 86 micromol/g or at least 200 micromol/g, ligands. The ligand content of the sample application substrate can also be between 50 and 2000 micromol/g, such as between 86 and 2000 micromol/g, between 200 and 2000 micromol/g, between 900 and 2000 micromol/g or between 200 and 1000 micromol/g. In some embodiments the charged groups of the ligands are positively charged or negatively charged over at least part of the pH 5 to pH 9 interval, such as over at least part of the pH 6 to pH 8 interval. The ligands may also comprise both positively and negatively charged groups, e.g. amphoteric or zwitterionic groups.

In some embodiments the sample application substrate further comprises groups capable of non charge-charge interactions with at least one analyte. These non charge-charge interactions may e.g. comprise hydrophobic interactions, electron acceptor-donor interactions, and/or thiophilic interactions. The interactions may be achieved by e.g. a substrate comprising multi-modal ligands comprising charged groups.

In certain embodiments the ligands are covalently bound to cellulose or glass fibres. They may be bound directly to the fibres or via spacer or extender structures. The covalent bonds can be achieved e.g. by chemical coupling of the ligands to the fibres before the formation of the paper or to the fibres during post-treatment of a base paper.

In some embodiments the ligands further comprise one or more aromatic or heteroaromatic ring structures and/or C4-C18 saturated or unsaturated, linear, branched or alicyclic hydrocarbon chains, optionally substituted or interrupted by heteroatoms such as ether, hydroxyl or carbonyl oxygens, amine, quaternary ammonium or amide nitrogens and/or thioether, thiol or sulphonyl sulphurs. Specific examples of ligands with such structures are N-benzyl-N-methylethanolamine, N,N-dimethylbenzylamine and various alkylamines (e.g. coupled via the amine nitrogen), and ligands comprising an aromatic or heteroaromatic ring structure linked to a negatively charged group via a linker structure, e.g. N-benzoyl homocysteine (which may be coupled via the thiol group).

In one aspect the present invention discloses a method of preparing a functional paper which comprises the steps of
  a) providing a cellulose fibre pulp,
  b) reacting said fibre pulp with a ligand precursor reagent to obtain essentially intact fibres comprising covalently bound ligands,
  c) on a continuous-web paper machine forming a paper web comprising at least 90 wt % of the essentially intact fibres with covalently bound ligands (measured as dry weight).

The method is suitable for preparing sample application substrates that are useful in sample preservation and sample pre-treatment methods e.g. according to the embodiments described above. Advantages of the disclosed method are that high ligand contents can be achieved under conditions suitable for industrial manufacture, that a substrate with good mechanical properties and absorption properties for biological samples such as blood can be prepared and no physical handling of delicate wet paper soaked in reagent solutions is required. Continuous-web paper machines are the preferred equipment for manufacturing of paper on an industrial scale. An aqueous fibre pulp is continuously fed to a sieving cloth (wire), where a paper web is formed and dewatered. After continuous pressing and drying, the paper web is e.g. cut into reels for further processing. The properties of the paper produced are distinctly different from laboratory scale handsheets produced on various handsheet formers and the requirements on the fibre pulp are also more stringent for continuous-web paper machines in comparison with handsheet formers.

The fibre pulp can comprise plain, non-functional fibres or fibres that have been activated by treating them with an activating reagent before the reaction with the ligand precursor. Typical activating reagents are electrophiles able to react with hydroxyl groups in the fibres and producing a reactive group for subsequent reaction. Examples of activating reagents include epichlorohydrin and diepoxides (producing reactive epoxy groups), allyl glycidyl ether and allyl halides (producing reactive allyl groups), divinyl sulfone (producing reactive vinyl sulfone groups), tosyl and tresyl chlorides (producing reactive tosylates/tresylates) etc. Examples of ligand precursor reagents able to react directly with hydroxyl groups are organic halides, e.g. diethylaminoethyl chloride, 2-bromoethane sulphonic acid sodium salt and 2-bromoacetic acid; epoxides, e.g. glycidyl trimethylammonium chloride and reactive vinyls, e.g. vinyl sulphonic acid sodium salt. Examples of ligand precursor reagents able to react with epoxies, vinyl sulfones and tosylates/tresylates on activated fibres include e.g. amines and thiols. Examples of ligand precursor reagents able to react with allyls on activated fibres includes e.g. thiols and polymerizable unsaturated monomers. Polymerizable monomers comprising charged groups may be graft polymerized onto the fibres either by copolymerization with allyls or other unsaturated groups on the fibres, by chain transfer reactions to e.g. thiols on the fibres or by intitiation from the fibres, e.g. in cerium grafting or ATRP grafting methods.

In certain embodiments the fibre pulp is in step b) reacted with the ligand precursor reagent to obtain essentially intact fibres comprising at least 50 micromol/g, such as at least 86 micromol/g or at least 200 micromol/g, covalently bound ligands.

In some embodiments the paper web formed in step c) comprises at least 96 wt %, such as at least 98 or 99 wt % of the essentially intact fibres with covalently bound ligands. As the fibres are essentially intact (i.e. they retain their fibrous structure without excessive fines formation in comparison to non-modified fibres), the mechanical properties of the modified fibres are good enough that no non-modified reinforcing fibres need to be added. An advantage of this is that all the surfaces in the paper substrate are available for interactions with sample components.

In certain embodiments, the ligand precursor reagent used in step b) is an electrophilic reagent and the reaction takes place in the presence of about 1-10 wt % alkali, such as about 2-8% alkali. Alkali is needed to promote the reaction between hydroxyl groups and the reagent, but it is advantageous to avoid too high alkali concentrations in order to prevent physical and/or chemical degradation of the fibres. It is also advantageous to avoid acid reaction conditions as they generally cause degradation of the cellulose.

In some embodiments the ligands comprise charged groups. An advantage of this is that the functional paper is highly suitable as a sample application substrate in the sample preservation methods described in other embodiments above.

In some embodiments the ligands comprise one or more aromatic or heteroaromatic ring structures and/or C4-C18 saturated or unsaturated, linear, branched or alicyclic hydrocarbon chains, optionally substituted or interrupted by heteroatoms such as ether, hydroxyl or carbonyl oxygens, amine or amide nitrogens and/or thioether, thiol or sulphonyl sulphurs.

In certain embodiments the method further comprises a step d), where the paper web is cut into at least one sample application card, and a step e) where at least one designated sample application area is printed and/or embossed on the paper web. These steps can be performed in any order after step c) and lead to the manufacture of a sample application substrate useful for the sample preservation methods described earlier in other embodiments.

The fibre pulp may comprise high purity cotton cellulose. However, it can also be of other materials such as delignified wood pulp and/or recycled paper. The starting material may be a ready formed cotton cellulose paper such as that known as 31ETF, a cotton cellulose paper, containing a small amount of hydrochloric acid (to contribute to wet strength) available from Whatman, part of GE Healthcare. The ready formed paper will require to be initially fibrillated for use in the method of the invention. Alternatively, cellulose fibres can be used directly before they are subjected to any paper making process.

Preferably, the fibrillation is carried out on raw cellulose fibres in e.g. a refiner or beater to the degree required for the intended paper structure by working the fibres bearing in mind the desired fibre length in the finished product. The treated material can be formed into sheets by conventional continuous-web papermaking techniques, for example using a mould, Fourdrinier or twin wire paper machine. To obtain a paper sheet of high purity, purified demineralised water can be used throughout the papermaking process. The paper produced can e.g. have a dry weight of 175 to 195 g/m2 and a thickness of 470 to 570 microns (at a gauge pressure of 53 kPa).

EXAMPLES

Example 1—Coupling of Diethylaminoethyl (DEAE) Groups on Cellulose Fibres 250 g of 31ETF (cotton cellulose paper available from Whatman, part of GE Healthcare) was fibrillated by dispersion in 2500 ml of demineralised water followed by addition of 268 ml of 47% w/w sodium hydroxide. After mixing for 15 minutes, 275 ml of 65% w/w aqueous diethylaminoethyl chloride hydrochloride was added and the mixture heated to 33 to 35 degrees C. and mixed for 1 hour. The resultant mixture was filtered, washed and tested for introduction of positively charged groups, ionic capacity and water content.

The ionic capacity of the fibres was assessed by titration to be 0.27 mmol/g with a water content (of the fibre) of 8.4%.

The fibres were successfully made into handsheets as described in Example 2.

Example 2—DEAE Paper Handsheets 4 to 4.5 g (dry weight) of conjugated fibre was dispersed in 1000 ml of demineralised water and blended for between 30 seconds and 1 minute. The resultant mix was poured into a handsheet former that already contained approximately 10 liters of demineralised water and gently mixed. The resultant mix was allowed to settle for 20 to 30 seconds, then drained. The mesh base and wet fibre matrix were removed from the unit and blotted gently to remove excess water followed by drying of the matrix at 100 to 105 degrees C. to produce successful handsheets.

Example 3—Coupling of Diethylaminoethyl (DEAE) Groups on Cellulose Fibres 20 kg of 31ETF paper was dispersed in 200 liters of demineralised water, followed by addition of 21.4 liters of 47% w/w sodium hydroxide and mixing for 15 minutes. 22 liters of 65% w/w diethylaminoethyl chloride hydrochloride was then added and the mixture heated to 33 to 35 degrees C. and mixed for 1 hour. The mixture was centrifuged and washed and tested for successful conjugation, capacity and water content. The ionic capacity was 0.23 mmol/g and the water content 5.94%.

Example 4—DEAE Paper on Paper Machine 20 kg of the DEAE coupled fibre from Example 3 was dispersed as necessary in demineralised water and subjected to papermaking on a pilot-scale mould paper machine. There was obtained a uniform paper product capable of receiving uniform blood spots and with a chloride ion capacity within the range of 0.2 to 0.3 mmol/g.

Example 5—Preparation of 31-ETF Pulp

31-ETF paper (250 g, dry weight) was pulped in a macerator (kitchen blender) with demineralised water. The pulp was filtered on a Buchner funnel to remove excess water and used without further modification or analysis.

Example 6—Preparation of Sulphoxyethyl Cellulose

To a 10-liter flange flask was added 527 g of pulped 31-ETF fibre (dry weight about 125 g). Propan-2-ol (5 liters) was added and the pulp stirred using a Heidolph RZR 2041 overhead stirrer for 10 minutes. 107 ml aqueous NaOH (47% w/v) was added and the mixture allowed to stir for a further 10 minutes. 22 g 2-bromoethane sulphonic acid sodium salt (0.1 mol.) was added portion-wise to the stirring solution. The reaction was heated to reflux using an Electrothermal iso-mantle for 30 minutes (80-84° C. internal temperature). The reaction was allowed to cool to RT whilst stirring continuously. The solid was filtered on a Buchner funnel and washed with demineralised water until a neutral pH was obtained.

Example 7—Preparation of Sulphoxyethyl Cellulose Handsheets

To macerator was added sulphoxyethyl cellulose (4.4 g) and demineralised water (1 L) and macerated for 30 seconds. The resulting pulp was formed into a handsheet using a handsheet former. The handsheet was blotted dry then oven dried overnight (100° C.). Analysis data: $H^+$ ion capacity by titration 0.45 mmol/g, 9.24% $H_2O$ content.

Example 8—Interaction of Methylene Blue Positively Charged Dye with Sulphoxyethyl Cellulose A disk (47 mm diameter) was acquired from the sulphoxyethyl cellulose handsheet described in Example 7. 1 ml aqueous methylene blue (0.157 mmol/L) was transferred to the centre of the disk, housed in an aluminium planchet (isotope analysis tray), using a Gilson pipette. The samples were dried in an oven (15 minutes, 100° C.) and placed in a desiccator overnight. The disks containing the dye were placed in separate plastic jars and demineralised water (10 ml) was added using a burette, the jars hand shaken for 15 seconds and shaken for a further 15 seconds prior to analysis. The 662 nm absorbance was measured on the supernatant, using a Pharmacia Biotech Ultrospec 2000 UV/Vis spectrophotometer.

Example 9—Interaction of Methylene Blue Dye with DEAE Cellulose

A disk (47 mm diameter) was acquired from the DEAE cellulose paper produced in Example 4. 1 ml aqueous methylene blue (0.157 mmol/L) was transferred to the centre of the disk, housed in an aluminium planchet, using a Gilson pipette. The samples were dried in an oven (15 minutes, 100° C.) and placed in a desiccator overnight. The disks containing the dye were placed in separate plastic jars, demineralised water (10 ml) added using a burette, the jars hand shaken for 15 seconds and shaken for a further 15 seconds prior to analysis. The 662 nm absorbance was measured on the supernatant, using a Pharmacia Biotech Ultrospec 2000 UV/Vis spectrophotometer.

Example 10—Interaction of Methylene Blue Dye with Non-Modified Cellulose (31-ETF)

A disk (47 mm diameter) was acquired from 31-ETF paper (Reel #: 955273, Furnish #: 9570). 1 ml aqueous methylene blue (0.157 mmol/L) was transferred to the centre of the disk, housed in an aluminium planchet, using a Gilson pipette. The samples were dried in an oven (15 minutes, 100° C.) and placed in a desiccator overnight. The disks containing the dye were placed in separate plastic jars, demineralised water (10 ml) added using a burette, the jars hand shaken for 15 seconds and shaken for a further 15 seconds prior to analysis. The 662 nm absorbance was measured on the supernatant, using a Pharmacia Biotech Ultrospec 2000 UV/Vis spectrophotometer.

Example 11—Interaction of Orange 2 Negatively Charged Dye with Sulphoxyethyl Cellulose A disk (47 mm diameter) was acquired from the sulphoxyethyl cellulose hand-sheet described in Example 7. 1 ml aqueous Orange 2 (CAS No. 6410-09-9, 0.142 mmol/L) was transferred to the centre of the disk, housed in an aluminium Planchet, using a Gilson pipette. The samples were dried in an oven (15 minutes, 100° C.) and placed in a desiccator overnight. The disks containing the dye were placed in separate plastic jars, demineralised water (10 ml) added using a burette, the jars hand shaken for 15 seconds and shaken for a further 15 seconds prior to analysis. The 485 nm absorbance was measured on the supernatant, using a Pharmacia Biotech Ultrospec 2000 UV/Vis spectrophotometer.

Example 12—Interaction of Orange 2 Dye with DEAE Cellulose

A disk (47 mm diameter) was acquired from DEAE cellulose paper produced in Example 4. 1 ml aqueous Orange 2 (0.142 mmol/L) was transferred to the centre of the disk, housed in an aluminium Planchet, using a Gilson pipette. The samples were dried in an oven (15 minutes, 100° C.) and placed in a desiccator overnight. The disks containing the dye were placed in separate plastic jars, demineralised water (10 ml) added using a burette, the jars hand shaken for 15 seconds and shaken for a further 15 seconds prior to analysis. The 485 nm absorbance was measured on the supernatant, using a Pharmacia Biotech Ultrospec 2000 UV/Vis spectrophotometer.

Example 13—Interaction of Orange 2 Dye with Non-Modified Cellulose (31-ETF)

A disk (47 mm diameter) was acquired from 31-ETF paper (Reel #: 955273, Furnish #: 9570). 1 ml aqueous Orange 2 (0.142 mmol/L) was transferred to the centre of the disk, housed in an aluminium Planchet, using a Gilson pipette. The samples were dried in an oven (15 minutes, 100° C.) and placed in a desiccator overnight. The disks containing the dye were placed in separate plastic jars, demineralised water (10 ml) added using a burette, the jars hand shaken for 15 seconds and shaken for a further 15 seconds prior to analysis. The 485 nm absorbance was measured on the supernatant, using a Pharmacia Biotech Ultrospec 2000 UV/Vis spectrophotometer.

Example 14—Recovery of a Positively Charged Analyte

Table 1 shows the results of the interaction of methylene blue with the chemically modified substrates (Examples 8 and 9).

TABLE 1

The % recovery of Methylene Blue (representing a positively charged analyte) from SE and DEAE cellulose after extraction with demineralised water.

| | Extraction 1 (15 mins) | Extraction 2 (75 mins) | Extraction 3 (75 mins) |
|---|---|---|---|
| Sulphoxyethyl Cellulose (SE) | 3.9% | 3.3% | 7.2% |
| Diethylaminoethyl Cellulose (DEAE) | 18.4% | 28% | 28.6% |

From the extraction method outlined above, an increase in recovery of the analyte is observed on both the chemically modified fibres. This recovery is further increased upon immersing the fibres in the extraction solvent for a longer period of time. To determine whether the extraction yield was dependent upon the length of time that the substrates were immersed in water a separate investigation was undertaken employing un-modified 31-ETF fibre as the benchmark (Examples 9 and 10). The results of which are provided in Table 2.

TABLE 2

Study to determine the % recovery of Methylene Blue over time.

| | Extraction 1 (60 mins) | Extraction 2 (120 mins) | Extraction 3 (300 mins) |
|---|---|---|---|
| 31-ETF | 7.3% | 6.2% | 3.2% |
| Diethylaminoethyl Cellulose | 33.8% | 37.5% | 37.2% |

The extraction time does not appear to have had a significant impact upon the recovery of the analyte.

However, during these experiments it was noted that the DE substrate was absorbing a significant quantity of the extraction solvent ($H_2O$). A further investigation was carried out to determine whether the volume of water added to extract the dye was of sufficient volume to perform the extraction without being absorbed by the substrate.

To verify this theory a 0.316 mmol/L and 1.57 mmol/L solution of methylene blue was added to the surface of the disks. The results provided in Table 3 indicate a significant increase in the recovery of methylene blue to 70% compared to the 31-ETF benchmark of 20%.

TABLE 3

Dye concentration study

| | Extraction 1 (0.316 mmol/L) | Extraction 2 (1.57 mmol/L) |
|---|---|---|
| 31-ETF | 6% | 20.3% |
| Diethylaminoethyl Cellulose | 31.8% | 69.9% |

Figure 1:
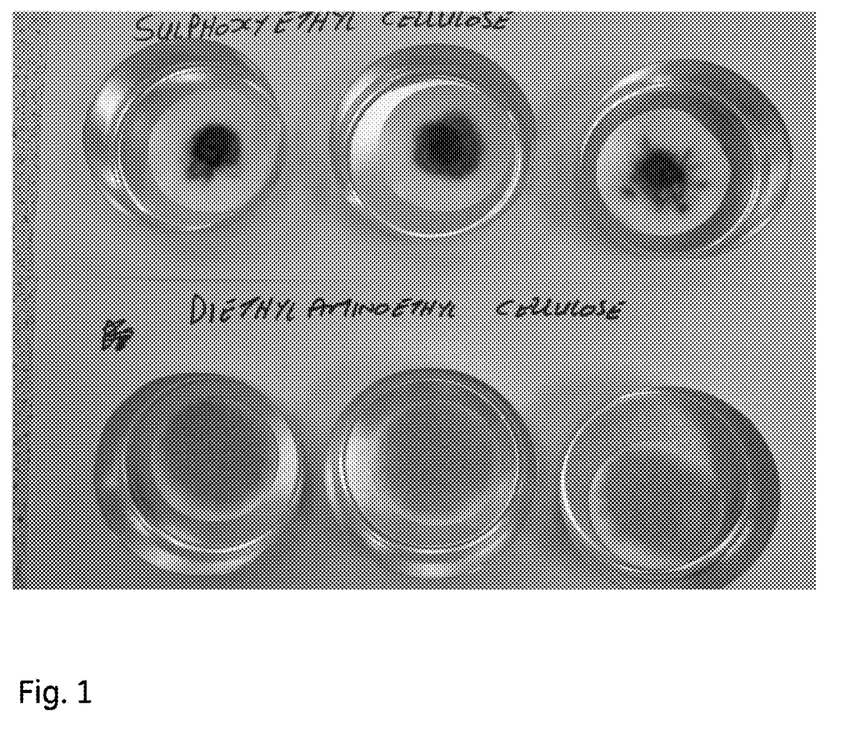
FIG. 1 shows the distribution of methylene blue dye in spots applied to papers with different ligands according to the invention.
Figure 3:
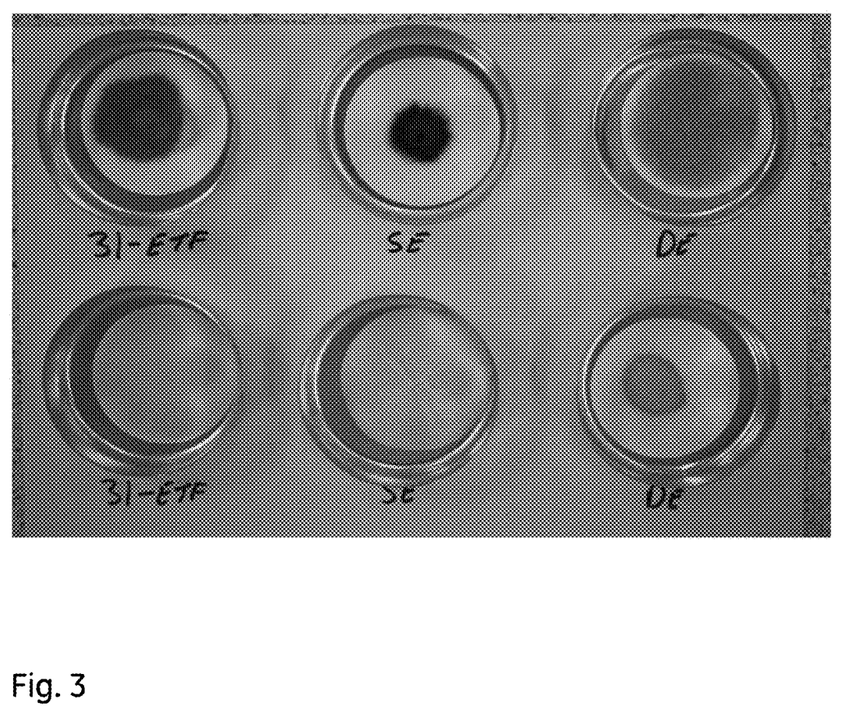
FIG. 3 shows the distribution of methylene blue and Orange 2 dyes in spots applied to papers with and without ligands.

The addition of methylene blue to both the SE and DEAE substrates has a significant impact upon the surface of the paper. FIG. 1 shows the dispersion of the dye on both chemically modified fibres. On SE cellulose the positively charged dye was concentrated in a pattern over the central part of the spot, while it dispersed homogeneously over the DEAE cellulose substrate. On the non-treated 31-ETF substrate a pattern was formed similar to the SE cellulose substrate (FIG. 3).

Example 15—Recovery of a Negatively Charged Analyte

As described previously, the dye Orange 2 was employed to represent a negatively charged analyte. The experimental procedure for this study was identical to that previously described for the positively charged analyte.

Table 4 clearly shows that the recovery of a negatively charged analyte from a negatively charged substrate exceeds the 75% target of analyte extraction. Interestingly, following identical extraction procedures no recovery of the analyte was observed for the positively charged substrate.

TABLE 4

The % recovery of Orange 2 (representing a negatively charged analyte) from SE and DEAE cellulose after extraction with demineralised water.

| | Extraction 1 (60 mins) | Extraction 2 (60 mins) | Extraction 3 (60 mins) |
|---|---|---|---|
| Sulphoxyethyl Cellulose (SE) | 83.8% | 81.9% | 84.8% |
| Diethylaminoethyl Cellulose (DEAE) | 0% | 0% | 0% |

Figure 2:
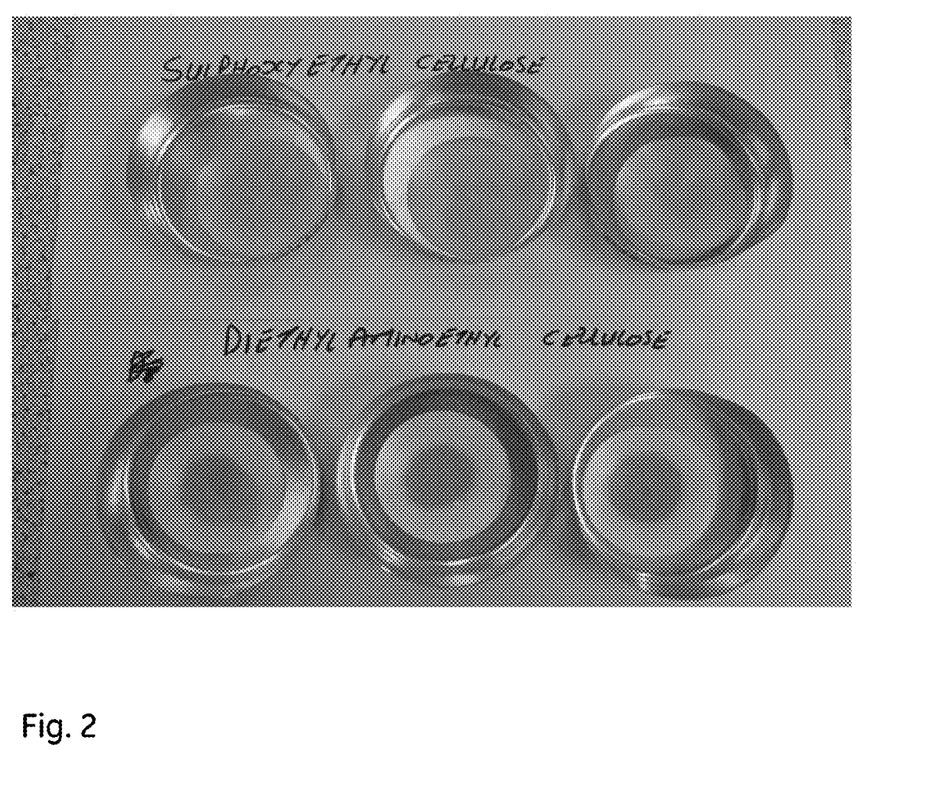
FIG. 2 shows the distribution of Orange 2 dye in spots applied to papers with different ligands according to the invention.

For illustrative purposes FIG. 2 provides a visual comparison of orange 2 on the surface of both a negatively and a positively charged substrate. The centrically concentrated colour observed on the DEAE substrate is again consistent with the extraction data provided previously, while the colour is homogeneously distributed over the SE cellulose substrate. The colour distribution on the untreated 31-ETF paper is somewhat more centric than on the SE cellulose.

Example 16—Retention of Phospholipids on Substrates

The clinical and pharmaceutical industries are seeking to significantly reduce the workflow of the DBS technique by reducing the time required to clean up the sample prior to analysis.

To facilitate this requirement, this example studies the ability of the ionic fibres to bind the undesirable materials in blood that interfere with the mass spec analysis, more specifically it focuses upon the retention of phospholipids on the substrates.

Asolectin which was used throughout this study is a mixture of phospholipids obtained from soybean, available e.g. as article 11145 from Sigma Aldrich. As described in Example 14, a 0.2% w/v of Asolectin in $CHCl_3$ (1 ml) was added to the centre of each disk and allowed to dry. Mass spectral analysis was carried out by punching a 5 mm hole from the centre of each substrate and extracting in MeOH:$CH_2Cl_2$ (70:30).

1 ml asolectin solution (0.2% w/v) in $CHCl_3$ was transferred via a Gilson pipette to the surface (47 mm diameter) of each substrate (SE, DEAE, 31-ETF) and allowed to dry in air at ambient temperature. A hole punch (5 mm) was taken from each disk and shaken in a glass vial for 15 seconds containing MeOH:$CH_2Cl_2$ (2 ml, 70:30), prior to mass spectral analysis, using a High Resolution Kratos Concept-IS±0.001 Daltons in positive-ion mode.

Figure 4:
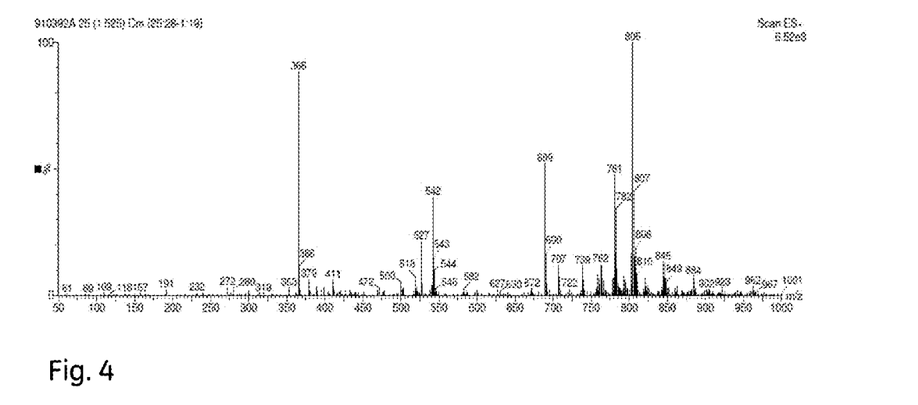
FIG. 4 shows a positive-ion mass spectrum of asolectin (a mixture of phospholipids).
Figure 5:
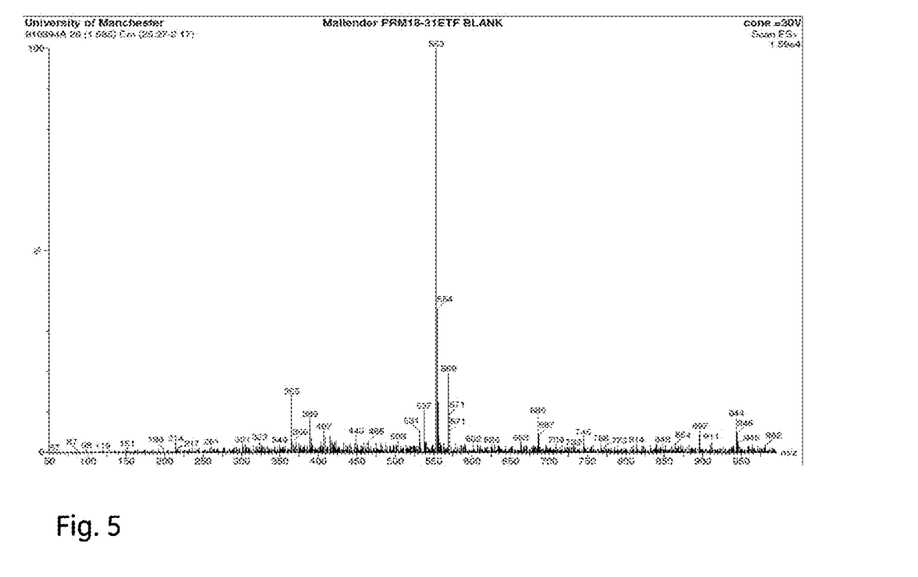
FIG. 5 shows a positive-ion mass spectrum of cellulose fibres (31-ETF) washed with MeOH:$CH_2Cl_2$ (70:30)

FIGS. 4&5 provide the mass spectra of both the Asolectin used in this study and the unmodified benchmark 31-ETF, respectively.

The spectrum of Asolectin illustrated in FIG. 4, shows peaks >10% abundance at m/z=365, 518, 527, 542, 689, 707, 739, 762, 781, 805, 845.

As mentioned previously, FIG. 5 provides the spectrum of our benchmark study. Unmodified 31-ETF shows peaks >10% abundance at m/z=365, 553, 569, 686, 944.

Figure 6:
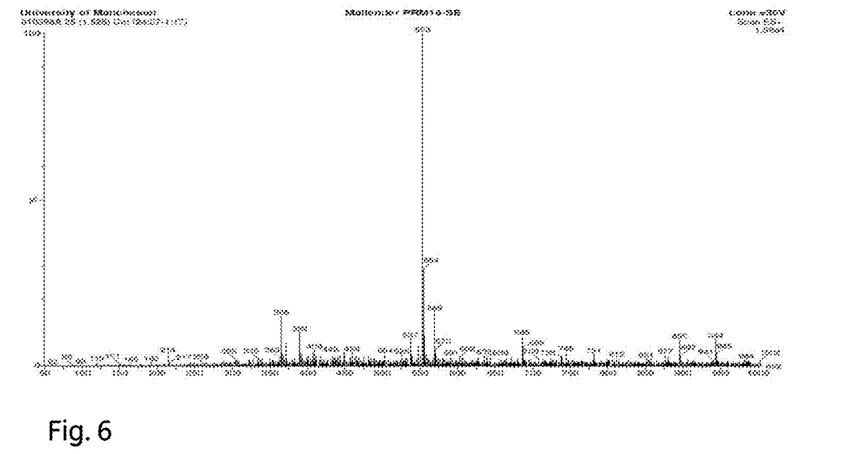
FIG. 6 shows a positive-ion mass spectrum of sulphoxyethyl cellulose substrate having ligands according to the invention+asolectin washed with MeOH:$CH_2Cl_2$ (70:30).
Figure 7:
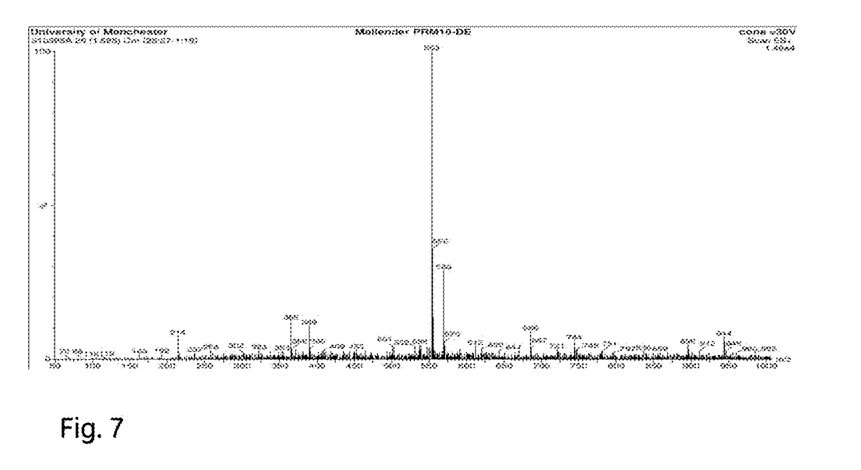
FIG. 7 shows a positive-ion mass spectrum of DEAE cellulose substrate having ligands according to the invention+asolectin washed with MeOH:$CH_2Cl_2$ (70:30).

These peaks are consistent with those observed in the spectra of the asolectin impregnated substrates of sulphoxyethyl cellulose, diethylaminoethyl cellulose in FIGS. 6 and 7 respectively and can attributed to the fragmentation of cellulose fibres.

The mass spectra of all the substrates do not show peaks that are consistent with those of asolectin. This study infers that phospholipids are being retained on the substrates and are not being extracted following the protocol outlined in Experiment 14.

Example 17—Recovery of Proteins from Dried Blood Spots

Human blood (~4.5 mL) was drawn in an EDTA treated Vacutainer tube. From this tube 995 microL blood was drawn and transferred to an Eppendorf tube containing 5 microL (5 microg/microL) of the fluorescent antibody ECL Plex Goat-α-Mouse IgG-Cy5 (GE Healthcare). The tube was then rotated gently allowing the antibody to mix with the blood for about 5 minutes.

Five reference papers Whatman FTA DMPK-C, Whatman #903 Protein Saver Card, Whatman Protran BA85 (all GE Healthcare), Munktell TFN (Munktell) and Ahlstrom 226 (Ahlstrom) were spotted in triplicate with the spiked blood (15 μL) together with the covalently modified prototypes. The papers were then dried at room temperature for approximately 2 h. The dried blood spots were punched from the paper yielding 12 mm discs which were placed in 1.5 mL tubes and 500 microL PBS-T buffer (PBS with 0.05% Tween 20) was added. The samples were shaken over night on a Heidolph Unimax 1010 shaker at ~190 rpm. After ~20 h the shaking was terminated and the discs removed from the tubes and left to dry at room temperature for 2 h before Typhoon analysis. The extraction solutions were spotted (5 μL) on the backside of a #903 card, analysed directly with the Typhoon and quantified from a set of similarly spotted standard solutions of ECL Plex Goat-α-Mouse IgG-Cy5.

TABLE 4

Recovery of IgG-Cy5 antibody from dried blood spots

| Substrate | Recovery of IgG-Cy5 (ng) |
|---|---|
| SE cellulose paper (example 7) | 3.1 |
| DEAE cellulose paper (example 4) | 3.7 |
| 31ETF | 3.1 |
| 903 | 2.6 |
| TFN | 3.2 |
| 226 | 2.4 |

The papers were also spotted with unspiked blood, dried and extracted as above, after which the human transferring content in the extracts were measured using a Bethyl Laboratories Inc Human Transferrin ELISA kit with an ELISA Starter Accessory Package (art. No. Cat No E80-128 and E101) according to the instructions of the supplier.

TABLE 5

Recovery of Transferrin from dried blood spots

| Substrate | Recovery of Transferrin (ng) |
|---|---|
| SE cellulose paper (example 7) | 2.7 |
| DEAE cellulose paper (example 4) | 3.4 |
| 31ETF | 3.1 |
| 903 | 2.7 |
| TFN | 2.8 |
| 226 | 2.5 |

The DEAE cellulose paper and two reference papers were also subjected to evaluation using a synthetic model system which was applied on the papers as 15 μL spots. The spot solution contained Cy5-IgG antibody (i.e. ECL Plex goat-α-mouse IgG-Cy5 antibody, GE Healthcare—labelled with Cy5 fluorescent dye, 25 ng/μL), Transferrin (25 ng/μL), BSA (50 mg/mL) and water. The dried spots were extracted over night at room temperature with PBS-T (PBS buffer with 0.05% Tween 20) and analysed using Typhoon image densitometry (Typhoon fluorescence scanner, GE Healthcare) and ELISA.

TABLE 6

Recovery of IgG-Cy5 antibody from protein solution spots

| Substrate | Recovery of IgG-Cy5 (ng) |
|---|---|
| DEAE cellulose paper (example 4) | 5.1 |
| DMPK-C | 4.1 |
| 903 | 3.5 |

Example 18—Epichlorohydrin (ECH) and Allyl Glycidylether (AGE) Activation of Paper a) ECH Activation Filter paper sheets 8×5 cm were rolled with a polyethylene spacer net and put in a Bellco Spinner Flask (150 ml) and a mixture of NaOH (50%, 9.9 ml) and demineralised water (96 ml) was added to the flask. After about 5 minutes of stirring ECH (15 ml) was added to the flask and vigorous stirring begun. The reaction solution was then heated to 30° C. and left stirring for about 2-2.5 hours. The reactions were then stopped and the paper sheets washed in the flask by removing the reaction solution and adding water. This was then repeated four times, with around 30 minutes between the washes. These papers were then used immediately for further ligand coupling.

b) AGE Activation

Filter paper sheets 8×5 cm were rolled with a polyethylene spacer net and put in a Bellco Spinner Flask (150 ml) to which NaOH (2M, 100 ml) was added and stirring begun. After 30 minutes some of the NaOH solution (35 ml) was removed and AGE (65 ml) was added to the flask. The reaction solution was then heated to 50° C. and left with vigorous stirring over night. The reaction was stopped after about 20 hours and the paper sheets washed in the flask by removing the reaction solution and adding water (120 ml, left for 5 minutes) followed by EtOH (120 ml, left for 20 minutes to wash out remaining AGE) and water (120 ml×3, with 30 minutes between the washes). The paper sheets were dried at room temperature over night, tested for allyl groups with iodine staining and sent for elemental analysis.

Example 19—Coupling of Ligands to Activated Paper a) Coupling of N-Benzoyl Homocysteine Thiolactone N-benzoyl-DL-homocystein thiolactone (9.1 g, 35 mmol) was put in a flask along with water (100 ml) and NaOH (14.8 ml 50%-solution). The mixture was then heated to 40° C. and was left stirring for 4 hours. The pH of the solution was adjusted to 7-8 by adding HCl (avoiding pH levels lower than pH 7 where a white salt precipitated).

AGE activated paper sheets (Example 18b) were put in plastic Falcon tubes (50 ml). To the tubes were then added the hydrolysed ligand solution (above) and 2,2-Azobis(2-methylpropionamidine)hydrochloride (0.3 g, radical initiator). The tubes were put on a shaking table at 60° C. over night. After approximately 22 hours the reactions were stopped and the paper sheets washed with water in the tubes (5×50 ml, 30 minutes between each wash). The paper sheets were allowed to dry at room temperature over night. The dried paper sheets were analysed with elemental analysis. The nitrogen content was 1.29%, corresponding to a ligand content of 0.92 mmol/g dry paper.

N-benzoyl homocysteine with AGE-derived spacer attached to the sulphur.

b) Coupling of Benzylmethylethanolamine

ECH-activated paper sheets (Example 18a) were put in a Bellco Spinner Flask (150 ml). To the flask, water (109.5 ml) and N-benzyl-N-methylethanolamine (20.8 g, 20.5 ml) was added. After 5 minutes of stirring, NaOH (0.34 ml, 50%-solution) was added and the mixture heated to 40° C. The reaction was then left stirring at 40° C. over night. After approximately 20 hours the reactions were stopped and the paper sheets washed with water first one time in the flask and then four times in a crystallisation dish (200 ml×4, 20 minutes for each wash). The paper sheets were allowed to dry at room temperature over night. The dried paper sheets were analysed by elemental analysis and Metanil Yellow staining. The nitrogen content was 0.25%, corresponding to a ligand content of 0.18 mmol/g dry paper.

N-benzyl-N-methylethanolamine with ECH-derived spacer attached to the nitrogen c) Coupling of Heparin ECH-activated paper sheets (Example 18a) were put in a Bellco Spinner Flask (150 ml). To the flask, 6.5 g heparin in water (122 ml) and NaOH (8 ml, 50%-solution) was added. The reaction was allowed to proceed under stirring over night at 30° C. The paper sheets were then washed with water first one time in the flask and then four times in a crystallisation dish (200 ml×4, 20 minutes for each wash). The paper sheets were allowed to dry at room temperature over night.

d) Coupling of $NH_2$

ECH-activated paper sheets (Example 18a) were put in a Bellco Spinner Flask (150 ml). To the flask, 12.5% ammonia in water was added and the reaction was allowed to proceed under stirring over night at 30° C. The paper sheets were then washed with water first one time in the flask and then four times in a crystallisation dish (200 ml×4, 20 minutes for each wash). The paper sheets were allowed to dry at room temperature over night.

Example 20—Storage Stability

Modified and non-modified papers were spotted with blood and dried as in Example 17. After storage at either −20° C., +22° C. or +37° C. for different periods, paper samples were punched, extracted and analysed with respect to CRP (C-reactive protein) and human transferrin as in Example 17. CRP was determined using the Human CRP ELISA kit (cat. no. RH961CRP01HR) from BioVendor, according to the manufacturer's instructions.

TABLE 7

| Recoveries of CRP after storage | | | | | |
|---|---|---|---|---|---|
| Paper | −20° C., | +22° C., 10 days | +22° C., 4 weeks | +37° C., 3 days | +37° C., 4 weeks |
| 31ETF | 46.6% | 35.7% | 41.9% | 36.8% | 27.3% |
| 903 | 52.1% | 38.7% | 38.3% | 29.8% | 28.1% |
| TFN | 36.3% | 35.3% | 36.5% | 33.7% | 18.4% |
| 226 | 45.9% | 33.5% | 28.3% | 28.9% | 27.3% |
| N-benzoyl homo-cysteine | 61.0% | 52.6% | 54.7% | 52.3% | 41.3% |
| Heparin | 47.1% | 37.2% | 37.8% | 33.7% | 28.3% |
| N-benzyl-N-methyl-ethanolamine | 19.1% | 18.4% | 19.5% | 12.3% | 12.4% |
| $NH_2$ | 12.3% | 11.1% | 11.8% | 12.9% | 13.0% |

TABLE 8

Recoveries of transferrin after storage.

| Paper | −20° C. | +22° C., 10 days | +22° C., 4 weeks | +37° C., 4 weeks |
|---|---|---|---|---|
| 31ETF | 76.3% | 52.0% | 62.6% | 58.5% |
| 903 | 67.5% | 58.8% | 54.9% | 59.0% |
| TFN | 78.3% | 55.8% | 59.7% | 49.8% |
| 226 | 72.8% | 53.2% | 44.3% | 52.8% |
| N-benzoyl homocysteine | 89.7% | 78.7% | 59.4% | 73.2% |
| Heparin | 72.8% | 59.3% | 55.9% | 51.3% |
| N-benzyl-N-methylethanolamine | 76.1% | 66.4% | 55.0% | 53.9% |
| $NH_2$ | 67.2% | 56.0% | 50.9% | 52.2% |

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. Features of different embodiments and/or aspects of the invention may be combined to form further embodiments.

The invention claimed is:

1. A sample preservation method comprising the steps of:
    a) providing a paper substrate comprising ligands, wherein each said ligand is covalently bound to cellulose, wherein each said ligand comprises negatively charged groups and groups capable of hydrophobic interactions, and wherein said ligands are selected from N-benzyl-N-methylethanolamine, N,N-dimethylbenzylamine, N-benzoyl homocysteine, or any combination thereof;
    b) applying a sample comprising at least one analyte and at least one contaminant on said paper substrate, wherein said at least one analyte comprises a protein;
    c) drying said sample on said paper substrate;
    d) storing said paper substrate with said sample for at least 24 hours in order to preserve the sample for later analysis; and
    e) extracting at least part of said paper substrate to provide a solution of said analyte.

2. The sample preservation method of claim 1, further comprising after step c) a step c') of punching or cutting out a piece of predetermined area from said paper substrate with said sample and in step e) extracting said piece of predetermined area.

3. The sample preservation method of claim 1, further comprising a step c") of washing said paper substrate.

4. The sample preservation method of claim 1, wherein said sample comprises a biological fluid.

5. The sample preservation method of claim 1, wherein said at least one analyte is charged, with a net charge opposite the charged groups comprised in the ligands.

6. The sample preservation method of claim 1, wherein at least one contaminant comprises charged groups, with a net charge opposite to the charged groups comprised in the ligands.

7. The sample preservation method of claim 1, wherein step a) further comprises reacting a base paper with a ligand precursor reagent to provide said paper substrate comprising ligands.

8. The sample preservation method of claim 1, wherein step a) further comprises:
    a') reacting a fibre pulp with a ligand precursor reagent to obtain intact fibres comprising covalently bound ligands; and
    a") on a continuous-web paper machine forming a paper web comprising at least 90 weight (wt) % of said intact fibres with covalently bound ligands.

9. The sample preservation method of claim 1, wherein said paper substrate comprises at least 50 micromol/gram ligands.

10. The sample preservation method of claim 1, wherein said charged groups are negatively charged over at least part of a pH 5 to pH 9 interval.

11. The sample preservation method of claim 1, wherein said at least one analyte comprises a biopharmaceutical.

12. The sample preservation method of claim 1, wherein said ligands comprise N-benzoyl homocysteine.

13. The sample preservation method of claim 1, wherein said cellulose is activated by reaction with allylglycidyl ether.

14. The sample preservation method of claim 1, further comprising a step f) of analyzing said solution with respect to one or more of the concentration, structural integrity or biological activity of said analyte.

15. The sample preservation method of claim 14, wherein step f) comprises analyzing said solution by mass spectrometry, an immunoassay or a biological assay.

16. The sample preservation method of claim 14, wherein in the solution provided in step e), the ratio of said analyte concentration to the total concentration of contaminants is at least about twice as high as in said sample.

17. The sample preservation method of claim 1, wherein said contaminants comprise phospholipids.

18. The sample preservation method of claim 17, wherein in the solution provided in step e), the ratio of said analyte concentration to the total concentration of phospholipids is at least about twice as high as in said sample.

19. The sample preservation method of claim 1, wherein said paper substrate further comprises groups capable of non charge-charge interactions with at least one analyte.

20. The sample preservation method of claim 19, wherein said non charge-charge interactions comprise hydrophobic interactions, hydrogen bonding, thiophilic interactions, van der Waals interactions or cation-pi interactions.

* * * * *